(12) United States Patent
Brenowitz et al.

(10) Patent No.: US 9,880,173 B2
(45) Date of Patent: Jan. 30, 2018

(54) PYRITE SHRINK-FILM LAMINATE AS A HYDROXYL RADICAL GENERATOR

(71) Applicants: Albert Einstein College of Medicine of Yeshiva University, Bronx, NY (US); The Regents of the University of California, Oakland, CA (US)

(72) Inventors: Michael David Brenowitz, Chappaqua, NY (US); Matt Law, Irvine, CA (US); Michelle Khine, Irvine, CA (US)

(73) Assignees: ALBERT EINSTEIN COLLEGE OF MEDICINE, INC, Bronx, NY (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/980,408

(22) Filed: Dec. 28, 2015

(65) Prior Publication Data

US 2016/0187346 A1 Jun. 30, 2016

Related U.S. Application Data

(60) Provisional application No. 62/097,515, filed on Dec. 29, 2014.

(51) Int. Cl.
| | |
|---|---|
| *G01N 15/06* | (2006.01) |
| *G01N 33/00* | (2006.01) |
| *G01N 33/48* | (2006.01) |
| *G01N 33/68* | (2006.01) |
| *G01N 33/553* | (2006.01) |

(52) U.S. Cl.
CPC ....... *G01N 33/6803* (2013.01); *G01N 33/553* (2013.01)

(58) Field of Classification Search
CPC ......... B01J 10/00; G01N 15/06; G01N 33/00; G01N 33/48
USPC ...... 422/68.1, 547, 551, 552, 553, 554, 502, 422/503; 436/43, 86, 89, 94
See application file for complete search history.

(56) References Cited

U.S. PATENT DOCUMENTS

| | | | | |
|---|---|---|---|---|
| 2009/0087374 | A1* | 4/2009 | Schimek | B82Y 30/00 423/565 |
| 2011/0240108 | A1* | 10/2011 | Law | B82Y 30/00 136/255 |

(Continued)

*Primary Examiner* — Brian J Sines
(74) *Attorney, Agent, or Firm* — Knobbe, Martens, Olson & Bear, LLP (57) ABSTRACT

Disclosed are hydroxyl radial generating devices, comprising: a substrate layer; and a pyrite layer configured to produce hydroxyl radicals. Another aspect relates to a method for producing a hydroxyl radical generating device, comprising: providing a polymeric substrate layer; placing a layer of pyrite on a surface of the polymeric substrate layer to form a multi-layer structure; and applying heat to the multi-layer structure such that at least the surface of the polymeric substrate layer contracts; wherein the layer of pyrite contracts to a lesser extent than the surface of the polymeric substrate layer providing a textured surface comprising the pyrite layer. Also disclosed is a method of analysis, comprising: placing a solution comprising a biological substance on a sample site of a hydroxyl generating device comprising a surface of pyrite; incubating the solution; and analyzing a sample including proteolytic fragments of the biological substance.

7 Claims, 10 Drawing Sheets

(56) References Cited

U.S. PATENT DOCUMENTS

| | | | |
|---|---|---|---|
| 2013/0119346 A1* | 5/2013 | Huang | H01L 31/0264 257/21 |
| 2014/0205756 A1* | 7/2014 | Law | H01L 31/1864 427/374.1 |
| 2015/0270412 A1* | 9/2015 | Frantz | H01L 31/02167 136/256 |
| 2015/0340166 A1* | 11/2015 | Ren | H01G 9/2013 136/254 |
| 2016/0101988 A1* | 4/2016 | Law | B82Y 30/00 427/74 |

* cited by examiner

PYRITE SHRINK-FILM LAMINATE AS A HYDROXYL RADICAL GENERATOR

STATEMENT REGARDING FEDERALLY SPONSORED R&D

This project was supported by NSF-IDBR 0852796, the Bio-molecular Interaction Technologies Center, a NSF Industry/University Cooperative Research Center, NIH DP2 OD007283-01 and the U.S. DOE DE-EE0005324, funded by the SunShot Next Generation Photovoltaics II (NextGen PVII) program.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This application is directed at simple, easy to use, and low cost tools and methods for the analysis of biologics for pharmaceutical and other uses.

Description of the Related Art

Oxidative footprinting of proteins is typically carried out by synchrotron or gamma source radiolysis of water or laser photolysis of hydrogen peroxide. Both approaches require a sizable investment in infrastructure.

SUMMARY OF THE INVENTION

The structure of proteins, DNA and RNA and their complexes often dictates their biological function. In "footprinting", the solvent accessibility of the residues that constitute proteins and nucleic acids is determined from their reactivity to an exogenous reagent such as the hydroxyl radical (.OH). While .OH generation for protein footprinting can be achieved by radiolysis, photolysis and electrochemistry, we present simpler, lower cost, yet more elegant and more practical solutions. In some embodiments, an iron-bearing inorganic or organic film capable of providing $Fe^{2+}$ to react with $H_2O_2$, e.g., a thin film of pyrite (cubic $FeS_2$) nanocrystals deposited on a solid surface, in some approaches onto a shape memory polymer (e.g., a commodity shrink film of the type used in shrink-wrap applications) generates sufficient .OH via Fenton chemistry for oxidative footprinting analysis of biomolecules. The term shrink-wrap where used herein connotes the same or similar materials that are used in shrink-wrap applications, including shape memory polymers. We demonstrate that varying either time or $H_2O_2$ concentration yields the required .OH dose-oxidation response relationship provided in footprinting. A simple and scalable sample handling protocol is enabled by thermoforming the "pyrite shrink-film laminate" into a microtiter plate format. The low-cost and malleability of pyrite shrink-film laminate will facilitate its use in high throughput screening applications as well as integration into microfluidic devices.

Some embodiments relate to a hydroxyl radial generating device, comprising: a substrate layer; and a pyrite layer configured to produce .OH.

In some embodiments, the substrate layer comprises a material configured to shrink when heated by at least 50%, the pyrite layer configured to shrink when heated by a lesser amount such that when the substrate layer and the pyrite layer are shrunken the pyrite layer comprises a textured surface.

In some embodiments, the substrate layer and the pyrite layer are in a shrunken configuration.

In some embodiments, the hydroxyl radical generating device comprises at least one well for retaining a liquid sample.

In some embodiments, the hydroxyl radical generating device comprises a plurality of wells for retaining a plurality of liquid samples.

In some embodiments, the hydroxyl radical generating device comprises a microtiter plate comprising a plurality of sample wells, each of said wells having the pyrite layer therein.

In some embodiments, the hydroxyl radical generating device comprises a microfluidic device comprising at least one sample channel and a sample site in fluid communication with the sample channel, the sample site having the pyrite layer therein.

In some embodiments, the pyrite layer comprises pyrite crystals.

In some embodiments, the pyrite layer comprises nanoscale crystals.

In some embodiments, a shrunken configuration of the substrate layer has an area within a periphery thereof at a surface thereof that is at least 50% less than or even as much as 80% less than an area within the periphery at the surface in the pre-shrunk configuration.

In some embodiments, a shrunken configuration of the substrate layer has an area within a periphery thereof at a surface thereof that is at least 95% less than an area within the periphery at the surface in the pre-shrunk configuration.

Some embodiments relate to a method for producing a hydroxyl radical generating device, comprising: providing a polymeric substrate layer; placing a layer of pyrite on a surface of the polymeric substrate layer to form a multi-layer structure; and applying heat to the multi-layer structure such that at least the surface of the polymeric substrate layer contracts; wherein the layer of pyrite contacts to a lesser extent than the surface of the polymeric substrate layer providing a textured surface comprising the pyrite layer.

In some embodiments, the layer of pyrite comprise a layer of pyrite nanocrystals.

In some embodiments, after placing the layer of pyrite on the surface, the layer of pyrite comprises a minimum thickness of between 20 and 80 nm.

Some embodiments further comprise forming at least one sample site in the multi-layer structure.

Some embodiments further comprise thermoforming a well by heating the multi-layered structure above the glass transition temperature of the polymeric substrate layer and drawing the multi-layered structure into a sample site form.

In some embodiments, the sample site form comprises a structure comprising a plurality of openings and wherein drawing comprises deforming the multi-layer structure at each of the openings into the openings.

In some embodiments, applying heat causes a shrinkage of at least about 50% of the area of the surface.

In some embodiments, the layer of pyrite is deposited by a solution-based deposition method.

In some embodiments, the layer of pyrite is deposited by a gas-phase deposition method.

Some embodiments relate to a method of analysis, comprising: placing a solution comprising a biological substance on a sample site of a hydroxyl generating device comprising a surface of pyrite; incubating the solution; and analyzing a sample including proteolytic fragments of the biological substance.

Some embodiments further comprise performing drop deposition footprinting by placing the solution in a well of a microtiter plate and thereafter incubating and analyzing the sample.

Some embodiments further comprise placing the sample on a sample site of a microfluidic device and thereafter incubating and analyzing the sample.

In some embodiments, the surface of pyrite comprises a textured surface comprising nanocrystals.

Some embodiments further comprise combining an amount of $H_2O_2$ with the solution prior to incubating the solution.

Some embodiments further comprise incubating the solution by vibrating the sample test device and the solution.

Some embodiments further comprise combining the solution with a reaction halting medium after incubating.

Some embodiments further comprise activating a surface of a well prior to placing the solution therein.

In some embodiments, the biological substance includes DNA.

In some embodiments, the biological substance includes RNA, DNA, or one or more proteins.

In some embodiments, the biological substance includes one or more proteins.

Some embodiments relate to a kit for analyzing a sample, comprising: a substrate comprising a layer of pyrite disposed thereon; and one or more reagents that catalyze production of hydroxyl radicals from the layer of pyrite.

In some embodiments, the one or more reagents catalyze a Fenton chemical reaction.

In some embodiments, the one or more reagents comprise solution(s) of hydrogen peroxide ($H_2O_2$) and/or ascorbate.

In some embodiments, the substrate and pyrite layer comprise a portion of a microtiter plate.

In some embodiments, the substrate and pyrite layer comprise a portion of a microfluidic device.

In some embodiments, crystals are disposed, e.g., deposited, on a layer. A concentrating process such as heat-shrinking is used to create high surface area substrates for improved chemical reactions. The crystals can be nano-scale crystals in one example. Although pyrite is discussed in depth herein, the crystals can be other iron (e.g., iron oxide) or non-iron based compounds in certain embodiments.

In one embodiment, pyrite nanocrystals are deposited on shrink-film plastic. Heat is applied to the plastic to shrink the plastic. The result is a highly textured laminate surface. Wells are thermoformed into the surface. The wells can retain sample drops. The iron in the pyrite catalyzes the production of hydroxyl radicals by an efficient process, such as via Fenton chemistry.

This application describes an apparatus that is of great interest to the pharmaceutical industry. In one embodiment, the apparatus includes a pyrite shrink-film laminate. The pyrite shrink-film laminate can be used to generate hydroxyl radical for oxidative footprinting. Another apparatus is a bench top generator for producing hydroxyl radicals. The generator can be part of a kit that may include a pipette or other small volume dispenser.

In one embodiment a method is provided for producing an oxidative footprinting device. In the method, a polymeric substrate layer is provided. A layer of an iron-bearing inorganic or organic film capable of providing $Fe^{2+}$ to react with $H_2O_2$, e.g., pyrite, is placed on a surface of the polymeric substrate layer to form a multi-layer structure. Heat is applied to the multi-layer structure such that at least the surface of the polymeric substrate layer contracts. The layer of pyrite (or other inorganic or organic film capable of providing $Fe^{2+}$ to react with $H_2O_2$) contracts to a lesser extent than the surface of the polymeric substrate layer. This difference in contraction results in the pyrite layer buckling, providing a highly textured surface comprising the pyrite layer.

In another embodiment, a drop deposition footprinting method is provided. In the method, a solution comprising a biological substance is placed on a sample site of a sample test device comprising at least one well surrounded by a highly textured surface of pyrite (or other inorganic or organic film capable of providing $Fe^{2+}$ to react with $H_2O_2$). The solution is incubated. A sample including proteolytic fragments of the biological substance is analyzed.

In another embodiment, a hydroxyl radical generator is provided that includes a first layer and a second layer. The first layer comprises a material at a surface of the first layer. The surface is surrounded by a periphery. The first layer has pre-shrunk configuration and a shrunken configuration. The shrunken configuration has an area within the periphery at the surface that is less than, e.g., a least 50% less than, the area within the periphery at the surface in the pre-shrunk configuration. The second layer comprises a material configured to produce .OH in the presence of a biological sample. The second layer is configured to shrink to a lesser extent than the surface of the first layer within the periphery, such that the second layer is highly textured when the first layer is in the shrunken configuration.

The second layer in the foregoing embodiment can include an inorganic or organic film capable of providing $Fe^{2+}$ to react with $H_2O_2$, e.g., formed using pyrite. The pyrite can be in a nanocrystalline form.

In another embodiment, a microtiter plate is provided. The microtiter plate has a plurality of sample wells. At least one of the wells has a layer of pyrite therein. In other embodiments, the well or wells can include any inorganic or organic film capable of providing $Fe^{2+}$ to react with $H_2O_2$.

In another embodiment, a microfluidic device is provided. The microfluidic device comprises at least one sample channel and a sample site. The sample site is in fluid communication with the sample channel. The sample site can have a layer of pyrite therein. In other embodiments, the sample site can include any inorganic or organic film capable of providing $Fe^{2+}$ to react with $H_2O_2$.

In another embodiment, a kit is provided for making a bench top generator for producing hydroxyl radicals for molecular footprinting. The kit includes a shrinkable polymeric layer and a vial of any inorganic or organic substance capable of providing $Fe^{2+}$ to react with $H_2O_2$. The kit also includes a template for forming fluid channels or fluid wells.

The apparatuses and methods herein can be configured as diagnostic and research and development tools.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 5 shows relative .OH production assayed and quantitated by fluorescent dye degradation. (A) Quantification of .OH production by pyrite shrink-film laminate as a function of $H_2O_2$ and ascorbate concentration at constant 5 min incubation; (B) Three μL buffered solution drops containing dye and 8 mM $H_2O_2$ and 2 mM ascorbate were incubated on three different samples: a mineral pyrite surface, a pyrite nanocrystal film airbrushed onto a silicon wafer, and the pyrite shrink-film laminate. The samples were vibrated to aid mixing. The control samples contained the same solutes but were not incubated on pyrite; (C) Dose-response curves relating .OH generation by pyrite shrink-film laminate as a function of incubation time (solid line) and $H_2O_2$ concentration (dashed line) with 10 mM $H_2O_2$ and 2 mM ascorbate present in solution at a constant incubation time of 5 min.

FIG. 7 shows oxidation of the protein Programmed Death-1 (PD-1) by pyrite shrink laminate. Three μL of PD-1 in buffer containing 1 mM ascorbate and the indicated $H_2O_2$ concentration were incubated for 1 min with vibration on pyrite shrink-film laminate. Aliquots of the protein were proteolyzed and prepared for mass spectral analysis. Panel (A) provides a MALDI-MS1 analysis of the N-terminal tryptic peptide (residues 1-36) of PD-1 showing the multiples of +16 mass increases detected as a function of increasing concentrations of $H_2O_2$. Panel (B) provides the fraction of unmodified peptide as a function of $H_2O_2$ concentration. The solid line is an exponential fit to the data. The insert is a ribbon representation of the PD-1 structure highlighting the N-terminal peptide in green and the residues Y4, W8, W26, and M31 that are highly susceptible to oxidation.

FIG. 10. Contact with pyrite shrink laminate does not cause denaturation of PD-1. Drops containing PD-1 in standard reaction buffer were incubated on the surfaces for 25 min with vibration prior to analysis of the protein's global conformation. (A) Intrinsic tryptophan fluorescence was used to determine whether exposure of the protein PD-1 (□) to bare polyolefin (O) or pyrite shrink laminate (Δ) unfolds the protein. PD-1 denatured in 2 M urea (shaded ♦) is shown for comparison. (B) Sedimentation velocity analytical ultracentrifugation analysis measures the global conformation of biological macromolecules. The native conformation of PD-1 is maintained following exposure of the protein to bare polyolefin or pyrite shrink laminate is the invariance of the measured sedimentation (S) and diffusion coefficients (D). S and D are corrected to standard conditions (S20,w and D20,w) to account for temperature (20° C.) and buffer properties within the experiment.

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Introduction

In "footprinting," solvent accessibility of individual residues of biological macromolecules is measured by their reactivity to an exogenous reagent (V. Petri and M. Brenowitz 1997 *Current opinion in biotechnology* 8: 36-44; K. Takamoto and M. R. Chance 2006 *Annual review of biophysics and biomolecular structure* 35: 251-276). The hydroxyl radical (.OH) is an effective footprinting probe due to its high reactivity and small size (G. V. Buxton 1988 *J Phys Chem Ref Data* 17: 513-886). Nucleic acid .OH footprinting monitors backbone polysaccharide cleavage (T. D. Tullius and B. A. Dombroski, 1986 *Proceedings of the National Academy of Sciences of the United States of America* 83: 5469-5473). Mapping of DNA structure and protein binding (T. D. Tullius and B. A. Dombroski, 1986 *Proceedings of the National Academy of Sciences of the United States of America* 83: 5469-5473) was followed by study of RNA structure and folding (B. Sclavi et al. 1998 *Science* 279: 1940-1943). Quantification of side chain oxidation is the dominant mode of protein footprinting analyses (K. Takamoto and M. R. Chance 2006 *Annual review of* biophysics and biomolecular structure 35: 251-276). Footprinting isotherms and time progress curves linked to local structural transitions resolve macromolecular binding and folding mechanisms (M. Brenowitz et al. 2002 *Current opinion in structural biology* 12: 648-653).

Ascorbate-driven Fenton chemistry mediated by [Fe(edta)]$^{2-}$ is a widely used .OH footprinting method (T. D. Tullius and B. A. Dombroski, 1986 *Proceedings of the National Academy of Sciences of the United States of America* 83: 5469-5473). The coupled reactions are:

$$Fe^{2+}+H_2O_2 \rightarrow Fe^{3+}+HO.+OH^- \quad (1); and$$

$$Fe^{3+}+H_2O_2 \rightarrow Fe^{2+}+HOO.+H^+ \quad (2)$$

Variations include using reaction 1 alone to study fast structural transitions (I. Shcherbakova, S. et al. 2006 *Nucleic acids research* 34: e48), using dissolved $O_2$ instead of $H_2O_2$ (K. Takamoto et al. 2004 *Journal of molecular biology* 343: 1195-1206), and substituting peroxonitrous acid for [Fe(edta)]$^{2-}$ and $H_2O_2$ (P. A. King et al. 1993 *Nucleic acids research* 21: 2473-2478). Radiolysis of water using low flux gamma (J. J. Hayes et al. 1990 *Methods in enzymology* 186: 545-549) and high flux synchrotron radiation (B. Sclavi et al. 1997 *Journal of molecular biology* 266: 144-159; S. D. Maleknia et al. 1999 *Analytical chemis-try* 71: 3965-3973), a pulsed electron beam (C. Watson et al. 2009 *Analytical chemistry* 81: 2496-2505), laser photolysis of $H_2O_2$ (D. M. Hambly and M. L. Gross 2005 *Journal of the American Society for Mass Spectrometry* 16: 2057-2063) and electrochemical oxidation (E. B. Monroe and M. L. Heien 2013 *Analytical chemistry* 85: 6185-6189) are used to generate .OH for footprinting. The latter approaches require specialized equipment for radical generation, management of fluid flow and sample collection.

The mineral iron pyrite (cubic FeS$_2$) supports Fenton chemistry (C. A. Cohn et al. 2004 *Abstr Pap Am Chem S* 228: U698-U698). Powdered pyrite in a microfluidic device footprints DNA and RNA (J. C. Schlatterer and M. Brenowitz 2009 *Methods* 49: 142-147; J. C. Schlatterer et al. 2012 *Biochemical and biophysical research communications* 425: 374-378). However, powdered mineral proved incompatible with multiplexed microfluidic mixers (Jones, C D, Schlatterer, J C, Brenowitz, M & Pollack L; unpublished). Herein we describe the deposition of pyrite nanocrystals (J. Puthussery et al. 2011 *Journal of the American Chemical Society* 133: 716-719) onto shape memory polymer (e.g., commodity shrink film or a layer of film; D. Nguyen et al. 2010 *Lab on a chip* 10: 1623-1626) to create a novel mediator of Fenton chemistry. Thermally inducing the pyrite coated shrink film to retract causes the stiffer nanocrystalline layer to buckle resulting in a highly reactive, wrinkled and robustly integrated laminate of pyrite nanocrystals. Sample wells can be thermoformed into the laminate in a standard well format that enables footprinting studies to be carried out by the simple deposition and removal of sample drops. We demonstrate the utility of pyrite shrink-warp laminate for the controlled generation of .OH for the oxidative protein footprinting.

Materials and Methods

Fabrication and Characterization of Pyrite Shrink-Film Laminate

Figure 1:
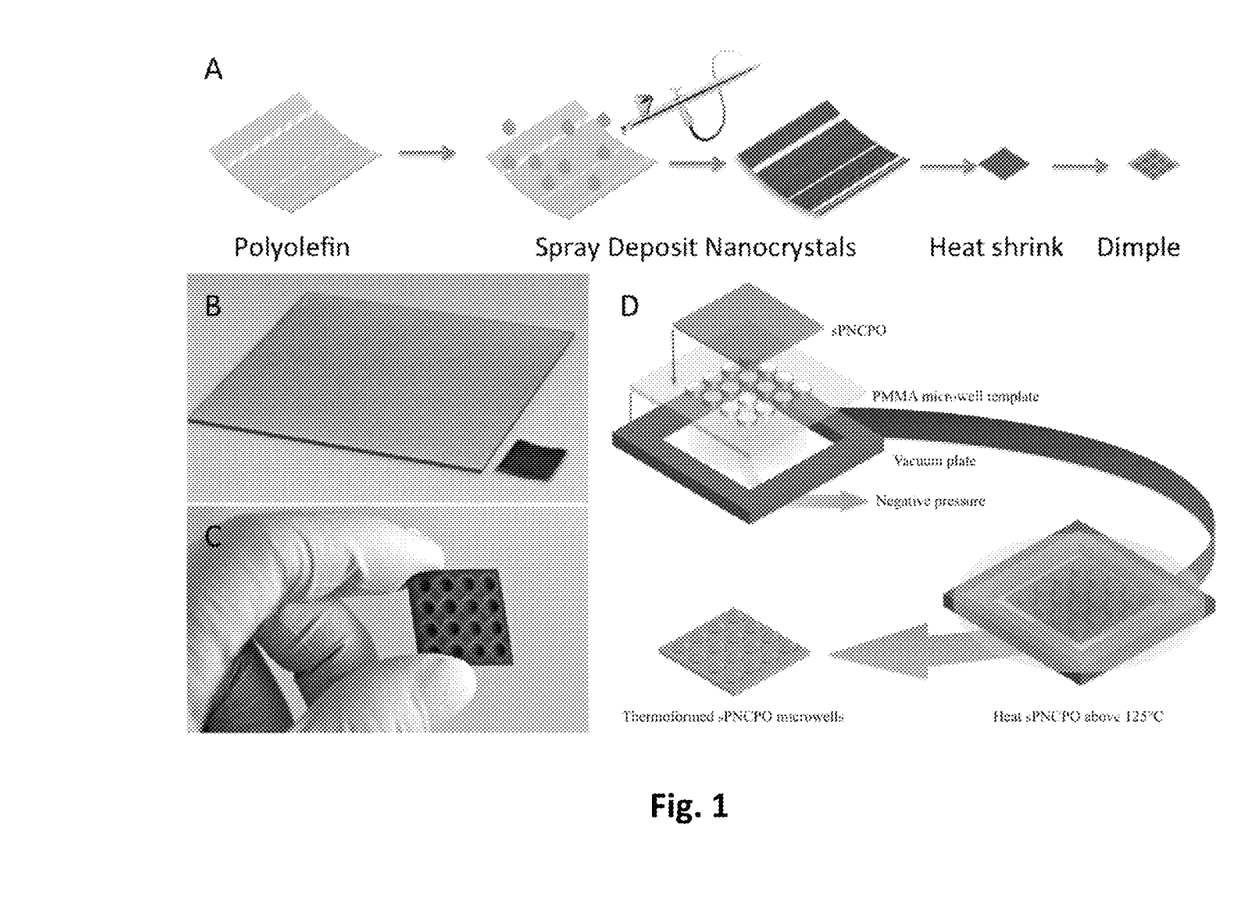
FIG. 1. (A) illustrates one method for fabricating an embodiment of a pyrite shrink-film laminate. (B) includes photographs of a substrate before (left) and after (right) thermal shrinking (C) shows an image of a substrate modified to include microwells. (D) shows a schematic of the process for thermoforming the laminate to form microwells.

Pyrite nanocrystals can be prepared via a hot-injection method based on a published synthesis (J. Puthussery et al. 2011 *Journal of the American Chemical Society* 133: 716-719) as detailed in the Examples. The pyrite colloidal suspension can be spray coated onto 4"×4" shape-memory polyolefin sheets (Cryovac D955, Sealed Air) using a hand-held Badger Model 200 airbrush (FIG. 1A). Polyolefin sheets can be pinned to PMMA substrates and mounted vertically in a fume hood. Spray coating is performed twice at room temperature with manual sweeps of ~3 s from 8" descending from top to bottom; 5 mL of suspension are consumed for each coat. Ligand exchange is not performed.

The coated polyolefin sheets are shrunk at 160° C. by waving a heat gun (HL 1810 S, Steinel) above its surface (FIG. 1A). The polyolefin quickly shrinks, e.g., by 95% (FIG. 1B; D. Nguyen et al. 2011 *Biomicrofluidics* 5: 22209). A weight such as one or more binder clips is attached to the corners to prevent the sheets from folding over. Microwells are thermoformed into the laminate (FIGS. 1, C & D) using a template patterned into 3 mm thick PMMA (McMaster-Carr) to 384 well plate specifications with a $CO_2$ laser cutter (Versalaser). Pyrite shrink-film laminate is placed on top of the template, a vacuum is applied and the laminate gently heated above the glass transition temperature of polyolefin (125° C.) with the heat gun. The negative pressure pulls the laminate into the template vias to form the microwells (FIG. 1D).

Figure 2:
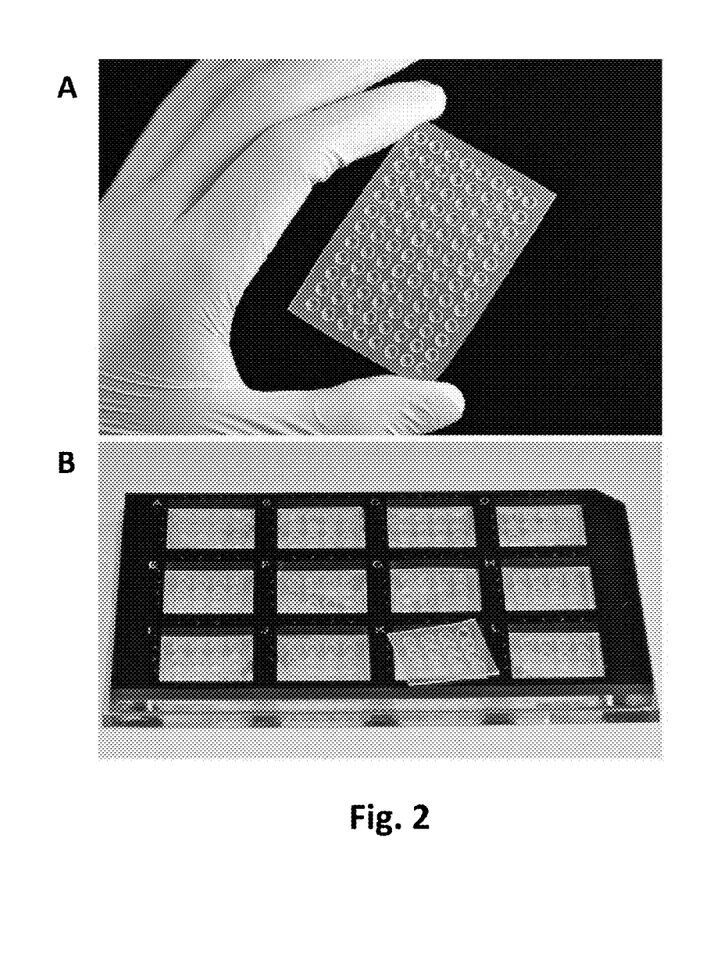
FIG. 2 (A) shows an example embodiment in which a microtiter plate is provided that includes an array of wells formed therein for testing samples. (B) illustrates a process in which the production of sample test devices can be scaled by providing for production more than one such device at the same time.

FIG. 2A shows a microtiter plate that can be produced in the process illustrated in FIGS. 1(a)-1(d). The microtiter plate can allow efficient testing in a plurality of wells formed in the plate. FIG. 2B illustrates that a scalable process can be used to produce many sample test devices at the same time. In one approach a forming plate is provided. The forming plate can have as many windows as sample test devices to be produced. In this case, there are twelve windows. But in variants there can be more than twelve, including more than 20, more than 50, more than 100 or more than 500 windows. A structure produced by the process illustrated in at least the left four images of FIG. 1(a) and FIG. 1(b) can be used to produce a plurality of concentrated surface layer structure, e.g., a concentrated laminate structures comprising a wrinkled pyrite surface. Each concentrated surface layer structure can be placed in a corresponding window and subject to negative pressure through a well or channel-forming template. The result can be plurality of sample test devices with wells or channels of desired depth or shape.

To measure Fe$^{2+}$ release from pyrite shrink-film laminate, 3 µL drops of solution containing 1 mM ascorbate and $H_2O_2$ at the indicated concentration are pipetted into wells and incubated with vibration for 60 s. The sample is collected and stock solutions of sodium acetate, hydroxylamine-HCl and 1,10'-phenanthroline are added to final concentrations of 120, 6, and 500 mM, respectively. The final volume of 1.2 mL is incubated, e.g., for 10 min at room temperature. The 508 nm absorption of the Fe$^{2+}$-1,10'-phenanthroline chelate is compared to a calibration curve constructed from known concentrations of ferrous ammonium sulfate hexahydrate (Sigma).

Drop Deposition Oxidation by Pyrite Shrink-Film Laminate

Figure 3:
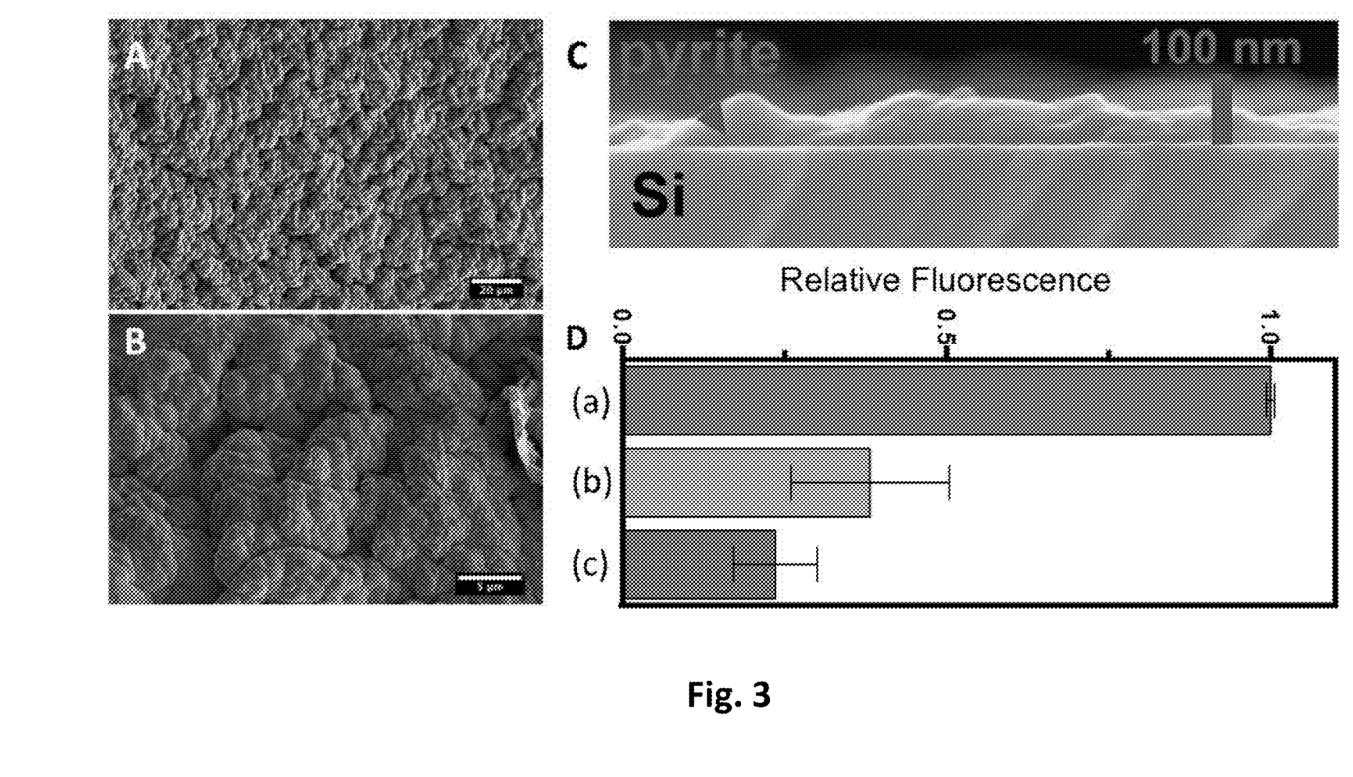
FIGS. 3 (A) and (B) are top down SEM images showing the high-surface-area pyrite micro-structure of laminate at medium and high resolution. (C) is a SEM image showing the cross-section of a pyrite nanocrystal film airbrushed onto silicon in a single pass. Although it is not used in some embodiments of the sample apparatus, the silicon substrate facilitates fracturing for cross sectional imaging of the pyrite nanocrystal film. (D) shows relative fluorescence of solution drops of 3 μL containing fluorescent dye, 2 mM ascorbate and 8 mM $H_2O_2$, which were incubated for 1 min in a microfuge tube (a), in a pyrite shrink-film microwell (b) and a pyrite microwell with vibration (c).

A 16 well pyrite shrink laminate chip (FIG. 1C) is affixed to a tabletop-mounted 6 V, 10,000 RPM vibration motor (Amico UPC 610-696811493, Amazon.com). Surface oxidation is removed by adding 5 µL of 0.1 M HCl to microwells for 5 min followed by several water washes to neutralize the acid (FIG. 3). Measurement of the fluorescence loss of an aromatic dye is a convenient way to assess relative rates of .OH production (Example 4)(I. Shcherbakova, S. et al. 2006 *Nucleic acids research* 34: e48; B. Ou et al. 2002 *Journal of agricultural and food chemistry* 50: 2772-2777; and F. Chen et al. 2002 *J. Phys. Chem.* 106: 9485-9490).

In our protein studies, PD-1 is diluted to 100 µM in standard reaction buffer prior to oxidation experiments. Aliquots of recombinant BirA tagged mouse Programmed Death 1 (PD-1) is dialyzed into standard reaction buffer (20 mM Sodium Cacodylate pH 8.0, 50 mM NaCl, 1 mM EDTA); assays to test the retention of the protein's native fold are described in Example 10.

Figure 4:
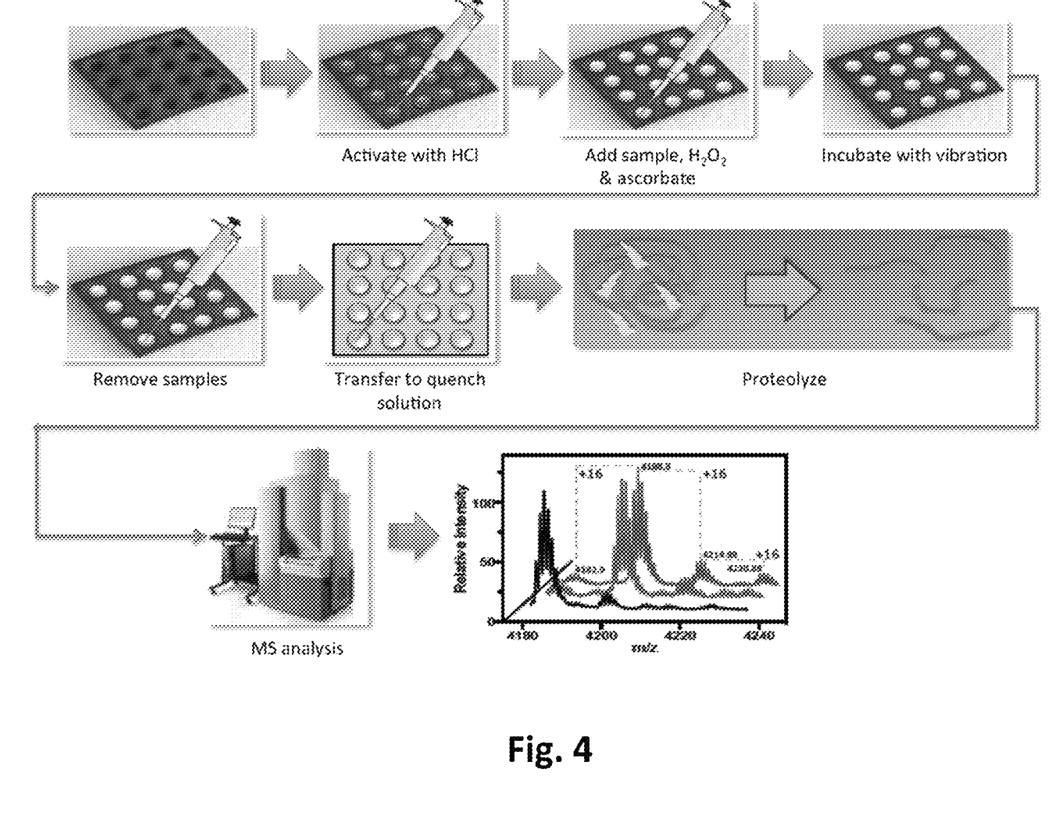
FIG. 4 illustrates a process flow summary for drop deposition oxidative footprinting, including some or all of the following stages: i) surface oxidation is removed by mild acid followed by pH neutralization with multiple water washes; ii) $H_2O_2$ and ascorbate are added to a protein sample in standard reaction buffer to the desired concentrations; iii) the reaction mixture is pipetted into microwell and incubated with vibration for a defined period of time; iv) the sample is transferred to the quench solution; v) aliquots are removed from the quenched sample for proteolytic fragmentation and mass spectral analysis. In variants that are not illustrated, multiple samples can be processed in parallel using manual or robotic multichannel pipettes with or without acid wash.

FIG. 4 illustrates one method of 'drop deposition oxidation'. Just prior to initiating oxidation, 0.6 and 2.4 µL of stock solutions of sodium ascorbate and $H_2O_2$, respectively are added to 27 µL of protein or dye in buffer to the desired concentrations. A 3 µL aliquot is pipetted into a pyrite shrink-film laminate microwell, vibration is provided (e.g., for 1 min), vibration is terminated and the sample pipetted to 27 µL of a 'quench solution' containing 34 µM thiourea, 12 µM methioninamide and 13 µg/mL catalase (G. Xu et al. 2005 *Analytical chemistry* 77: 3029-3037). Protein samples are snap frozen on dry ice and stored at −20° C. for analysis by mass spectrometry.

Standard protocols are used to prepare PD-1 for analysis by MALDI-TOF mass spectroscopy (Example 5). PD-1 is digested with trypsin and MALDI-TOF spectra from 800-5000 m/z are collected and normalized against the total peptide present in a sample. Protein Prospector (UCSF) is used to predict the peptide masses of the MALDI precursor ions. Peaks corresponding to unmodified and oxidized (+16, +32, +48, etc.) states of each peptide are visually identified. The fraction of unmodified peptide is calculated from the ratio of the normalized intensity of the unmodified peptide peaks to the sum of the intensities of both the unmodified and oxidized peaks of that peptide. Plotting the fraction of unmodified peptide against oxidation time or $H_2O_2$ concentration yields dose-response curves that are fit by non-linear regression in GraphPad Prism (M. Brenowitz et al. 2002 *Current opinion in structural biology* 12: 648-653).

Results
Fabrication and Characterization of Pyrite Shrink-Film Laminate

Pyrite nanocrystal colloidal suspension is easily sprayed on shape-memory polyolefin using an art supply airbrush (FIG. 1A). A single pass with the airbrush deposits a 50±25 nm thick coating (FIG. 3C). Two coats are applied. The sprayed layers are phase-pure pyrite as assayed by powder X-ray diffraction and Raman spectroscopy. The ~95% area reduction of shrunk shape-memory polyolefin (FIG. 1B) results in a 20 fold compression of the planar surface area. Top-down SEMs of laminates show wrinkling of the pyrite coating (FIGS. 3, A & B) similar to the wrinkling of metal thin films (D. Nawarathna et al. 2013 *Appl Phys Lett* 102: 63504). Cyclic voltammetry of gold films shows >600% increased surface area. We expect similar surface enhancement of the pyrite shrink laminate due to the similar surface topology (J. D. Pegan et al. 2013 *Lab on a chip*, 13: 4205-4209).

The microwells thermoformed into shrink-film laminate are patterned in the 384 well format and drawn to a depth sufficient to hold 3 µL (FIGS. 1C & D). Thermoforming the sample wells enables the simple sample handling protocol that we call 'drop deposition'. Sample handing is multiplexed with standard multi-channel pipettes.

Pyrite shrink-film laminate has properties that facilitate its use. The pyrite nanocrystalline coating integrates with the plastic during shrinkage, stabilizing the surface and thus preventing flaking or chipping. A 'tape test' performed on several laminate samples showed no visible transfer of pyrite from the laminates to the tape, demonstrating robust integration of the pyrite nanocrystals to the polyolefin. While a touch of a pipet tip does not disrupt the laminate surface, pyrite nanocrystals deposited on silicon are easily dislodged. Pyrite shrink-film laminate reproducibly generates .OH for ≥6 months when stored covered at ambient conditions.

Drop Deposition Oxidation

Figure 5:
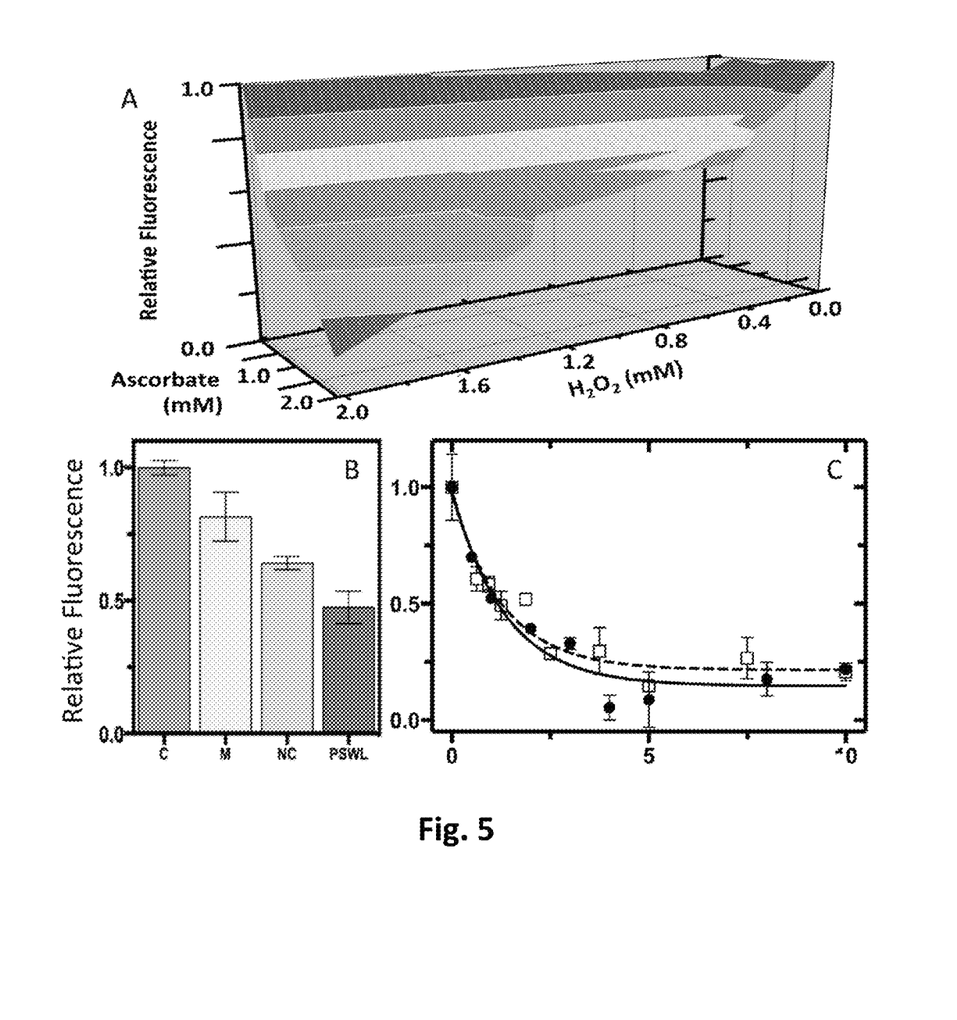

Optimization of .OH generation as a function of either time or $H_2O_2$ concentration was accomplished by quantifying the oxidation of the fluorescent dye fluorescein. In our protocol, 3 µL drops of sample solution are deposited, incubated and removed from the microwells (FIG. 3). The robust radical production evident for dye incubated with ascorbate and $H_2O_2$ on pyrite shrink-film laminate is enhanced by vibration during sample incubation, presumably by improving the sampling of the solution with the reactive surface (FIG. 3D). The increased oxidation observed comparing pyrite mineral, pyrite nanocrystals deposited on silicon, and pyrite shrink-film laminate shows that both the nanocrystalline form of pyrite and the wrinkled surface topology of the laminate both contribute to .OH production (FIG. 5B).

The production of .OH from pyrite shrink-film laminate was enhanced by systematically varying the concentrations of sodium ascorbate and $H_2O_2$. Excessive ascorbate reduces the .OH available to oxidize substrates since it is also a radical scavenger (B. Lipinski, Oxidative medicine and cellular longevity, 2011, 2011, 809696). One mM ascorbate maximizes .OH production as the $H_2O_2$ concentration is increased from 0 to 2 mM (FIG. 5A). We observe the exponential decay characteristic of a Poisson distribution with pyrite-shrink-film laminate when .OH production is controlled by either $H_2O_2$ concentration or incubation time (FIG. 5C). Achieving 'single-hit' distribution of modification or cleavage events is advantageous for quantitative footprinting (K. Takamoto and M. R. Chance 2006 *Annual review of biophysics and biomolecular structure* 35: 251-276; M. Brenowitz et al. 1986 *Methods in enzymology* 130: 132-181) and is conveniently achieved in our standard protocol by varying the $H_2O_2$ concentration at a constant time of 1 min.

Figure 6:
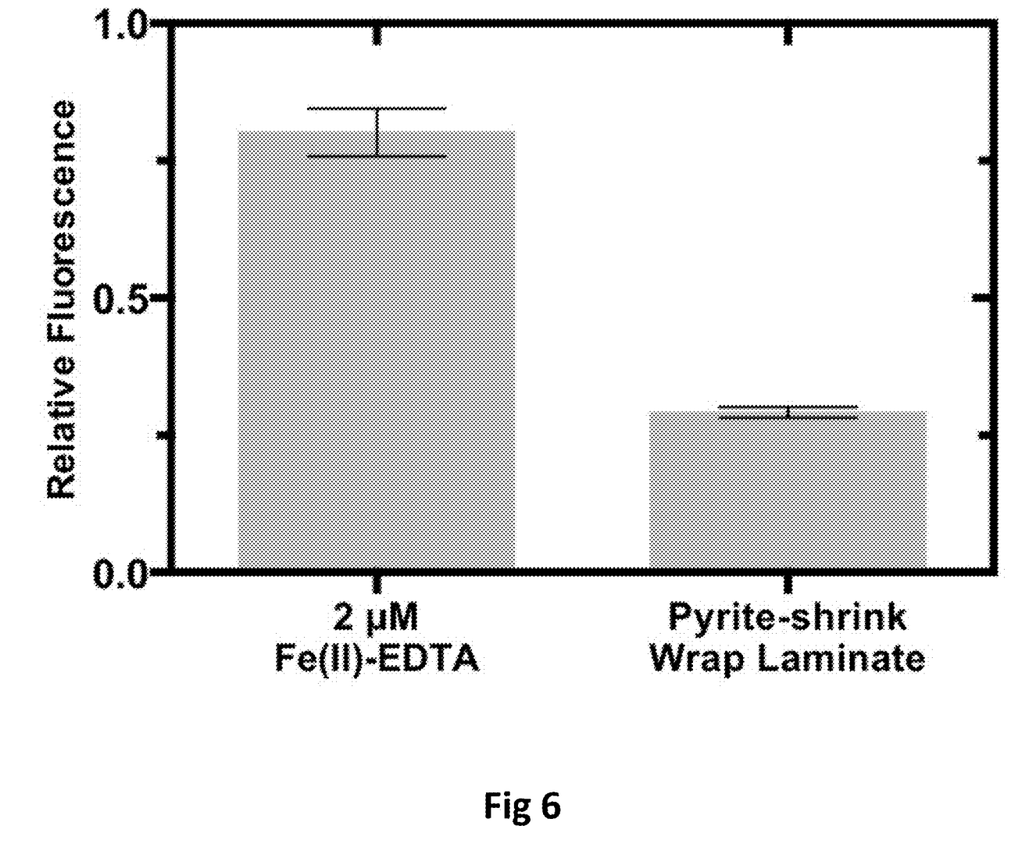
FIG. 6 shows a comparison of the relative oxidation by 2 μM Fe(II)-EDTA-[Fe(EDTA)]$^{2-}$—(roughly the amount of ferrous iron released into solution from pyrite shrink-film laminate) and the laminate itself. Two mM ascorbate with 15 mM $H_2O_2$ was present in both reactions that incubated for 1 min. Relative production of .OH was assayed by degradation of a fluorescent dye.
Figure 9:
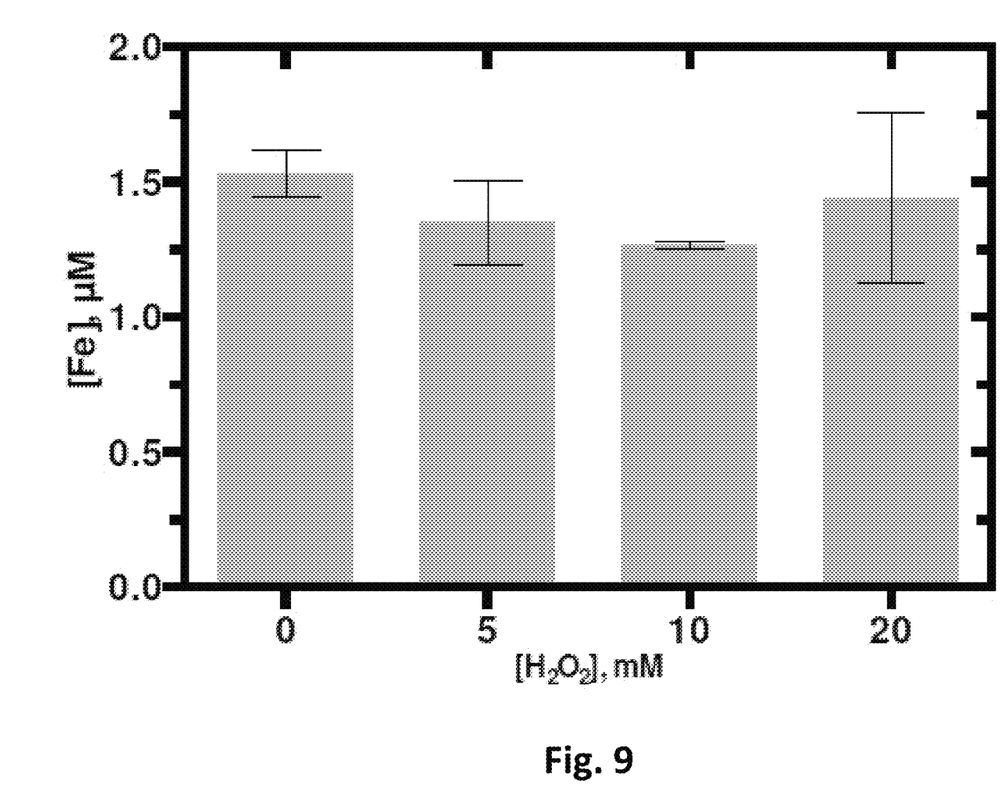
FIG. 9. Measurement of the amount of iron released from pyrite shrink-film laminate during production of .OH.
Figure 10:
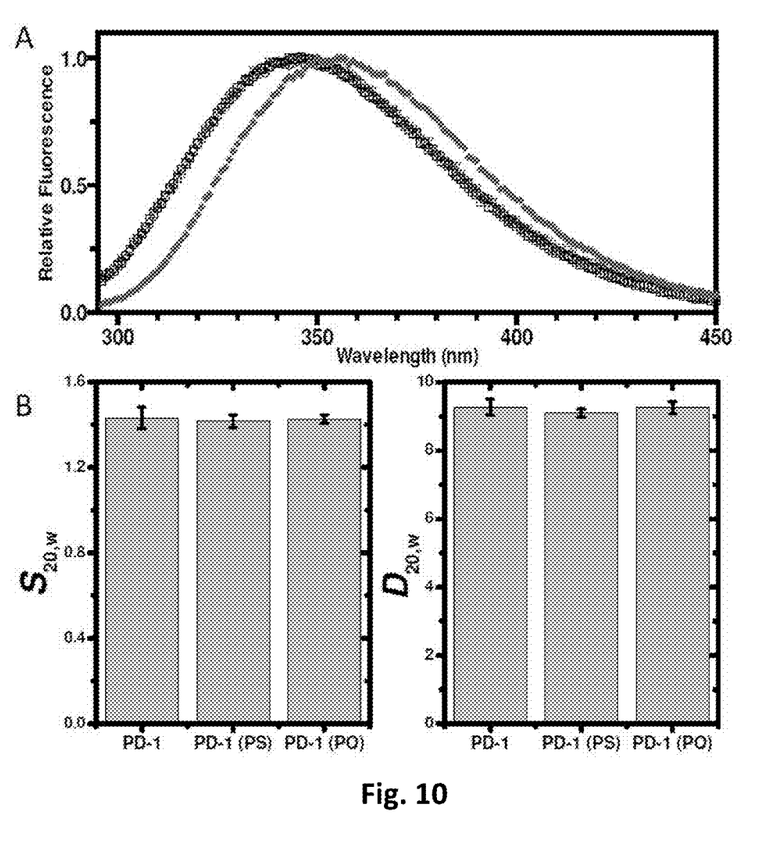

We measured the release of ferrous iron to determine if .OH production occurs exclusively on the nanocrystalline surface or also via dissolved ferrous iron. Independent of $H_2O_2$ concentration, 1.5 µM of iron is leached during the standard 1 min of incubation (FIG. 9). At common $H_2O_2$ and ascorbate concentrations and incubation time, pyrite shrink-film laminate produces substantially more oxidation than 2 µM $[Fe(edta)]^{2-}$ (FIG. 6), suggesting that the surface is the dominant source of .OH by pyrite shrink-film laminate.

Figure 7:
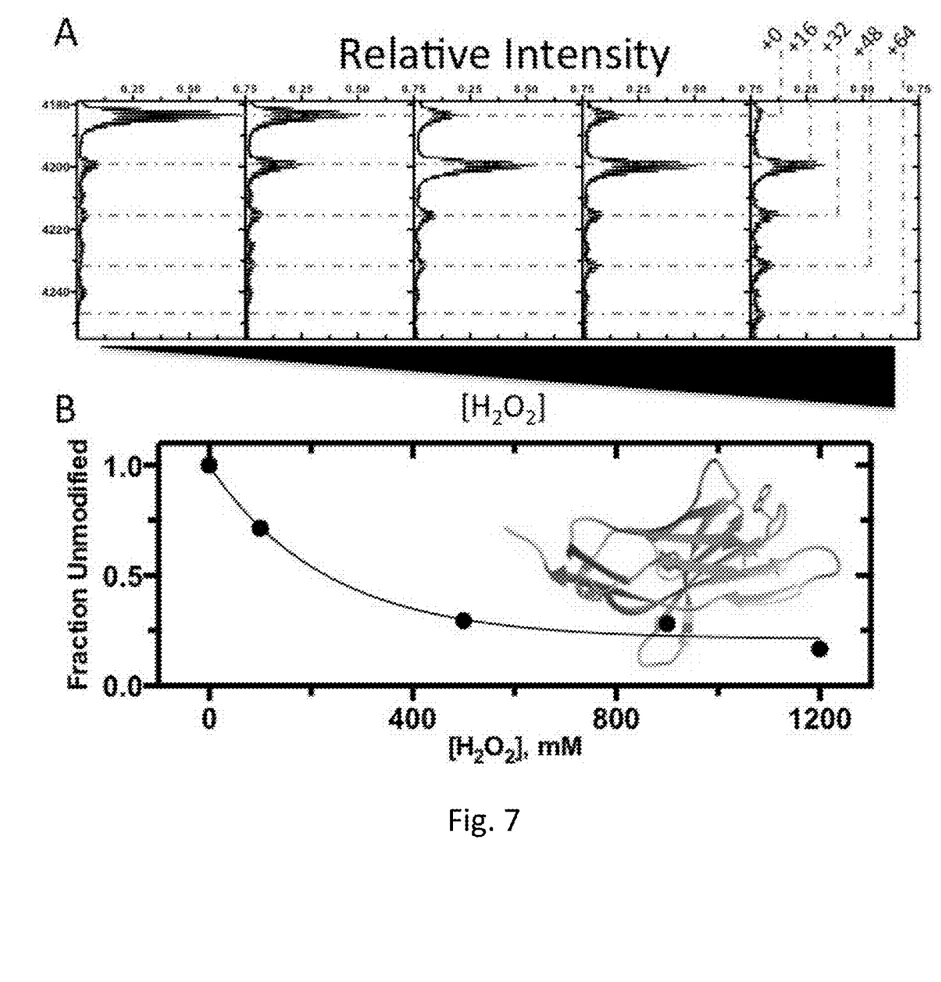
Figure 8:
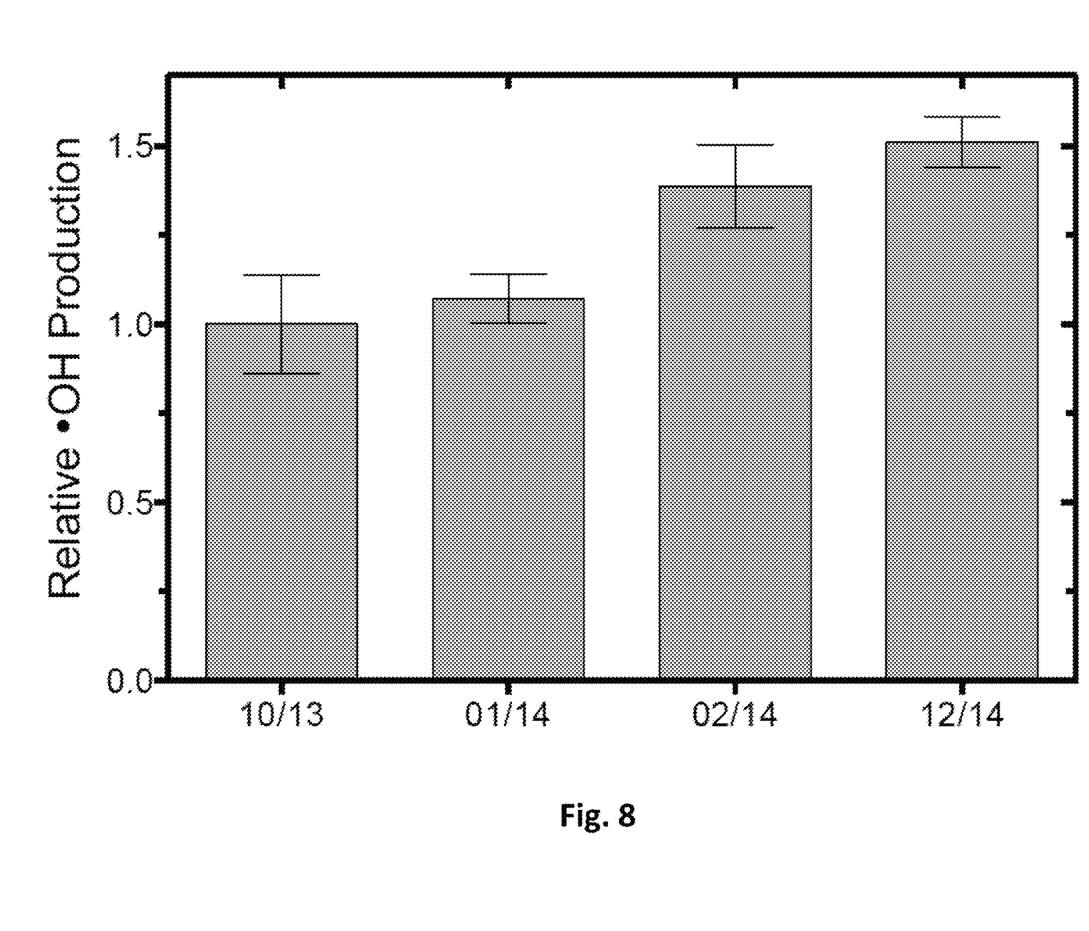
FIG. 8 shows the .OH production from pyrite shrink-film laminate as a function of storage time in a closed container at room temperature in the dark. Ambient humidity was quantified by the dye degradation assay conducted at constant experimental conditions. The data show that pyrite shrink-film laminate retains full activity when stored over the 14 months assayed. The data shown are normalized the first data point.

The PD-1 protein retains its native fold following exposure to either shrink plastic or pyrite shrink-film laminate (Example 10). PD-1 samples were incubated on pyrite-shrink-film laminate following our standard protocol as a function of $H_2O_2$ concentration and analyzed by MALDI (FIG. 3 & Example 5). MALDI is suitable for this study due to the protein's small size; peptides containing >90% of its sequence are detectable (data not shown). The N-terminal peptide (1-36) of PD-1 contains four residues susceptible to oxidation and accessible by solvent—Y4, W8, W26, and M31 (FIG. 7B, insert). The +16 ions and multiples thereof are evident as the .OH dose increases as a function of increasing $H_2O_2$ concentration (FIG. 7A). The overall oxidation of this peptide is well described by a Poisson distribution (FIG. 7B). Oxidation was extended beyond 'single-hit' in this illustration to demonstrate the efficacy of .OH generation (FIG. 7A). An oxidative footprinting analysis would utilize lower $H_2O_2$ concentrations to determine the modification rate and solvent accessibility and LC-MS/MS to isolate the oxidation of each of the susceptible residues.

Discussion

With the advent of protein therapeutics, there is an increased need to develop high throughput and facile methods to determine protein structure to support product development, validation and regulatory approval. While atomic resolution models of macromolecular complexes are the gold standard for structure, oxidative footprinting can contribute to the therapeutic development pipeline by rapidly and inexpensively mapping the molecular interfaces that mediate a biological activity. Our goal in creating pyrite shrink-film laminate is to lower the barrier to oxidative protein footprinting by eliminating the need for a source of ionizing radiation, a UV laser and/or microfluidic sample handling. Our apparatuses and methods can be implemented using simple, readily available equipment such as a standard laboratory pipette. Higher throughput can be achieved with a multi-channel pipette or robotic sample handler. Although $[Fe(edta)]^{2-}$ is routinely used in nucleic acid oxidative footprinting (T. D. Tullius and B. A. Dombroski, 1986 *Proceedings of the National Academy of Sciences of the United States of America* 83: 5469-5473), we have not achieved with this reagent the .OH dose consistency required for protein analysis (unpublished data). Pyrite can also be used to study of nucleic acids and their complexes with proteins (J. C. Schlatterer et al. 2012 *Biochemical and biophysical research communications* 425: 374-378).

Pyrite shrink-film laminate is easy and inexpensive to make. While the synthesis of pyrite nanocrystals requires expertise and an appropriately equipped laboratory, it is a straightforward and scalable process. Similarly scalable is the airbrush deposition of pyrite nanocrystals. Other methods for depositing pyrite films can also be used (e.g., electrodeposition and other low-temperature solution-based approaches). We have prepared prototype shrink-film pieces the size of a standard microtiter plate demonstrating a clear path to scaling up to support robotic sample handling systems. That pyrite shrink-film laminate can be stably stored will facilitate its adoption.

The laminate device is a promising apparatus for the development of a range of chemical reactions and microfluidic reactors due to bonding of the deposited material to the plastic and the enhanced surface area that results from shrinkage. Microwell fabrication is completely flexible. The number and volume of the wells is tailored by fabrication of a template of any suitable material, such as a PMMA template. Indeed, troughs, serpentine and branched patterns could be molded in the laminate for use in microfluidic applications. Other materials could be deposited that would facilitate or catalyze other chemical reactions. Thus, shrink-film laminate is a versatile platform with regard to both chemistry and physical configuration for the development of novel applications.

The effectiveness of pyrite shrink-film laminate is enhanced when the .OH dose can be precisely controlled allowing protein oxidation rates to be calculated. This characteristic, together with a scalable and customizable form factor will facilitate higher-throughput analysis without the need for infrastructure. We are applying our approach to the analysis of immunological recognition complexes. Complementary techniques that backbone solvent accessibility (H/DX 31, protein painting; A. Luchini et al. 2014 Nature communications 5: 4413) can be used concomitantly. A challenge to be addressed is the integration of multiple structural maps into robust models of molecular structure that can be applied to scientific discoveries and industrial processing applications.

Manufacturers of therapeutic antibodies and innovator and biosimilar biologics need to map the solvent accessible surface of their molecules as well as map their target epitopes. Our technology will enable a simple and less expensive way to accomplish these goals for development as well as regulatory analysis Our technology is of great interest to the pharmaceutical industry for the analysis of biologics as it is simple, easy to use and requires less material than the other footprinting techniques being applied.

The pyrite shrink-film laminate apparatuses discussed herein significantly reduce the cost of important pharmaceutical analyses including protein mapping analysis. For example, it is believed that these apparatuses will be advantageous for Fab-antigen and Mab-antigen complexes.

EXAMPLE 1

Deposition of Pyrite Nanocrystal Films on Shape-Memory or Other Heat Shrink Polymer All chemicals were used as received. Anhydrous iron (II) chloride (99.9% metal basis), sulfur powder (99.998%), anhydrous chloroform (≥99%), and anhydrous ethanol (99.5%) were purchased from Sigma Aldrich. Octadecylamine (90%) and diphenyl ether (99%) were purchased from Acros. All synthesis reactions were performed on a Schlenk line under air-free conditions. Briefly, a solution of 480 mg of sulfur in 10 mL of diphenyl ether was added to a solution of 368 mg of anhydrous $FeCl_2$ in 25 g of octadecylamine. Both precursor solutions were degassed at 75-85° C. for 1 hr and then placed under flowing Ar atmosphere. After heating the octadecylamine solution to 218° C., the ether solution was injected at 210° C. and the reaction stirred at 218° C. for 3 hr to grow the nanocrystals. The reaction was then quenched with a water bath. Once the solution temperature reached 95° C., 20 mL of ethanol was injected to prevent the octadecylamine from solidifying. The quenched solution was immediately centrifuged at 4,400 rpm for 3 min and the resulting precipitate dispersed in 30 mL of chloroform. The nanocrystals were purified by two additional rounds of precipitation in ethanol and redispersion in chloroform. A final centrifugation at 3,000 rpm for 2 min was performed to remove any aggregates from the nanocrystal suspension. The resulting colloids (6-8 mg/mL) are stable for up to 2 wks when stored in air.

EXAMPLE 2

Time Frame for Pyrite Shrink-Film Fabrication

The synthesis of the pyrite nanocrystals and the fabrication of pyrite shrink-film laminate take surprisingly little time. A total of eight and a half hours is required to fabricate eight 16-well chips (a total of 128 sample wells). The bulk of the time (7' 45") is for synthesis of the pyrite nanocrystals. Deposition of the nanocrystals, shrinking the coated polyolefin and thermoforming the sample wells requires an additional 45". It should be noted that fabrication of pyrite shrink-film laminate is amenable to scale up as all of the processes can be integrated into a roll-to-roll manufacturing line that would dramatically reduce the fabrication time per piece of pyrite shrink-film laminate.

EXAMPLE 3

Protein Preparation and Characterization

Aliquots of recombinant BirA tagged mouse Programmed Death 1 (PD-1) stored in 20 mM Tris-HCl, pH 8.0+150 mM NaCl were thawed and dialyzed into standard reaction buffer (20 mM Sodium Cacodylate pH 8.0, 50 mM NaCl, 1 mM EDTA) overnight at 4° C. Intrinsic fluorescence and sedimentation velocity analyses were performed to confirm that the protein retains its native fold. The intrinsic fluorescence of PD-1 was measured in a 3 mm quartz cuvette in a Fluoromax 3 spectrofluorometer in reaction buffer. Reference spectra for the denatured protein were obtained in this buffer to which 2 M guanidine was added (P. L. Privalov, *Critical reviews in biochemistry and molecular biology*, 1990, 25, 281-305). Sedimentation velocity analysis of PD-1 was conducted in a Beckman XL-I analytical ultracentrifuge in the Ti-60 rotor at 58,000 rpm and 20° C. using the absorption optics set to 280 nm. Values of the sedimentation and diffusion coefficients were calculated using the time-derivative method implemented in the program DCDT+ (J. S. Philo, *Anal Biochem*, 2006, 354, 238-246; W. F. Stafford, 3rd, *Anal Biochem*, 1992, 203, 295-301) and corrected to standard conditions (T. M. Laue et al. *The Royal Society of Chemistry*, Cambridge, UK, 1992, 90-125). The fluorescence and sedimentation properties of PD-1 were assayed before and after the protein was incubated within microwells drawn into either bare shrunk polyolefin or laminate (without $H_2O_2$ or ascorbate present).

EXAMPLE 4

Measurement of Oxidation by Fluorescent Dye Degradation

Measurement of the fluorescence loss of an aromatic dye in solution is a convenient way to assess relative rates of .OH production. This assay was conducted following published protocols (B. Ou, et al. *Journal of agricultural and food chemistry*, 2002, 50, 2772-2777; F. Chen, et al. *J. Phys. Chem.*, 2002, 106, 9485-9490 and I. Shcherbakova et al. *Nucleic acids research*, 2006, 34, e48). A stock solution of fluorescein (Molecular Probes, F1300) in standard reaction buffer was diluted such that the fluorescence of the final solution to be analyzed was within the linear dynamic range of a Spectramax M5 plate reader (490 nm excitation, 520 nm emission and 515 nm emission cutoff).

EXAMPLE 5

MALDI-TOF Mass Spectral Analysis of Protein Oxidation

One and one half µL of trypsin (sequence grade, Promega) was added to samples of either oxidized or unoxidized samples of PD-1 in the standard reaction buffer plus the quench solution that had been reduced using 98.5 µL of 0.02% proteaseMAX (Promega), 5 mM TCEP (Sigma), 20 mM iodoacetamide (Sigma) in 50 mM ammonium bicarbonate. A 1:20 ratio of trypsin to protein was added and digestion incubated for 3 hr at 37° C. with shaking. Decreasing the pH below 4 with 10% trifluoroacetic acid (TFA) terminates the reaction. Each digest was divided into aliquots, snap frozen on dry ice, and stored at −20° C. Individual volumes of each sample were concentrated and de-salted using C18 Zip-tips (Millipore). C18 tips were prepared using 100%, 50%, and 0% acetonitrile in the presence of 0.1% TFA. The sample aliquots were drawn into the resin to bind the peptides, followed by washing of the resin with 0.1% trifluoroacetic acid to remove salt, and finally eluted onto a MALDI plate using α-cyano-4-cinnamic acid in 70% acetonitrile/0.1% TFA.

EXAMPLE 6

Measurement of Iron Release from Pyrite Shrink-Film Laminate

To measure $Fe^{2+}$ release from pyrite shrink-film laminate, 3 µL drops of solution containing 1 mM ascorbate and $H_2O_2$ at the indicated concentration are pipetted into wells and incubated with vibration for 60 s. The sample is collected and stock solutions of sodium acetate, hydroxylamine-HCl and 1,10'-phenanthroline are added to final concentrations of 120, 6 and 500 mM, respectively. The final volume of 1.2 mL is incubated for 10 min at room temperature. The 508 nm absorption of the $Fe^{2+}$-1,10'-phenanthroline chelate is compared to a calibration curve constructed from known concentrations of ferrous ammonium sulfate hexahydrate (Sigma) (S. A. Kumar et al. *Analytica chimica acta*, 2014, 851, 87-94).

EXAMPLE 7

Hydroxyl Radical Generation Using $[Fe(Edta)]^{2-}$

Footprinting using $[Fe(edta)]^{2-}$ was conducted as described in (I. Shcherbakova et al. *Nucleic acids research*, 2006, 34, e48; E. Heyduk and T. Heyduk, *Biochemistry*, 1994, 33, 9643-9650). Briefly, dye was diluted to the desired concentration in the standard reaction buffer and 30 µL was aliquoted into a microfuge tube. Drops of 0.6 µL of fresh stock solutions of ascorbate, $H_2O_2$, and EDTA-$(NH_4)_2$Fe $(SO_4)_2 \cdot 6H_2O$ were added to final concentrations of 10 mM, 15 mM and 10 µM, respectively. Vortexing initiated oxidation, which was quenched after 1 min.

EXAMPLE 8

Pyrite Shrink-Film Laminate Stores Stably for at Least One Year

Hydroxyl radical (.OH) production from pyrite shrink-film laminate quantified as a function of storage time in a closed container at room temperature, in the dark and ambient humidity using the dye degradation assay described above at constant experimental conditions. A 3 µL drop containing dye, 8 mM $H_2O_2$ and 1 mM ascorbate was incubated with vibration for 60 sec and quenched following our standard protocol. The relative .OH production was normalized to the first measurement taken in October of 2013. Pyrite shrink-film laminate clearly does not lose activity when stored over the 14 months assayed.

EXAMPLE 9

Ferrous Iron Release from Pyrite Shrink-Film Laminate

Measurement of the amount of iron released from pyrite shrink-film laminate during production of .OH. Three µL buffered drops containing 1 mM ascorbate, and the indicated concentration of $H_2O_2$ was incubated on pyrite shrink-film for 1 min with vibration. The released ferrous iron was assayed by its chelation with 1,10'-phenanthroline as described above in this Supplement.

EXAMPLE 10

The Native Fold of PD-1 is Unaffected by Exposure to Either Bare Shrink-Film or Pyrite Shrink-Film Laminate Prior to demonstrating protein oxidation, control experiments were conducted to the PD-1 protein retains its native conformation following exposure to bare shrink plastic and pyrite shrink-film laminate surface (Supplementary FIG. 1). We verified that the protein is monomeric under our solution conditions by sedimentation equilibrium analysis (Mw=14,967±627 Da). Analytical sedimentation velocity reports the global conformation of a monodisperse protein; the sedimentation profiles of a control PD-1 sample and PD-1 incubated on bare shrink plastic or pyrite-shrink are indistinguishable; denatured protein would display slower sedimentation and diffusion rates. Intrinsic tryptophan fluorescence is an established measure of the stability of protein folds. When tryptophan residues move from a hydrophobic protein core toward solution, the emission maximum of tryptophan shifts to longer wavelengths. The emission spectra of PD-1 incubated on either material are indistinguishable from the control spectra that are readily distinguished from the spectra of the denatured protein. Two independent measures confirm that neither the plastic substrate nor pyrite shrink-film laminate surface denature the PD-1 protein.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A hydroxyl radial generating device, comprising:
   a substrate layer; and
   an iron-containing or non-iron containing inorganic or organic layer that provides $Fe^{2+}$ to react with $H_2O_2$ to produce •OH by Fenton chemistry,
   wherein the hydroxyl radical generating device comprises one or more wells configured to retain a liquid sample.

2. The hydroxyl radical generating device of claim 1, wherein the substrate layer comprises a heat-sensitive material that shrinks in size by at least 50% when heated, wherein the iron-containing or non-iron containing inorganic or organic layer is a pyrite layer that shrinks by a lesser amount when heated, such that when the substrate layer and the pyrite layer are shrunken the pyrite layer comprises a textured surface.

3. The hydroxyl radical generating device of claim 2, wherein the heat-sensitive substrate layer and the pyrite layer have been exposed to heat such that they are shrunken in size compared to before exposure to the heat.

4. The hydroxyl radical generating device of claim 1, wherein the hydroxyl radical generating device comprises a microtiter plate comprising a plurality of sample wells, each of said wells having the iron-containing or non-iron containing inorganic or organic layer therein.

5. A hydroxyl radial generating device, comprising:
   a substrate layer; and
   an iron-containing or non-iron containing inorganic or organic layer that provides $Fe^{2+}$ to react with $H_2O_2$ configured to produce .OH by Fenton chemistry,
   wherein the hydroxyl radical generating device comprises a microfluidic device comprising at least one sample channel and a sample site in fluid communication with the sample channel, the sample site having the iron-containing or non-iron containing inorganic or organic layer therein.

6. The hydroxyl radical generating device of claim 1, wherein the iron-containing or non-iron containing inorganic or organic layer comprises pyrite crystals.

7. The hydroxyl radical generating device of claim 1, wherein the iron-containing or non-iron containing inorganic or organic layer comprises nano-scale crystals of pyrite.

* * * * *